United States Patent [19]

Scholz

[11] Patent Number: 5,139,955

[45] Date of Patent: Aug. 18, 1992

[54] REAGENT, CELL AND METHOD FOR THE COULOMETRIC DETERMINATION OF WATER

[75] Inventor: Eugen Scholz, Garbsen, Fed. Rep. of Germany

[73] Assignee: Riedel-De Haen AG, Seelze, Fed. Rep. of Germany

[21] Appl. No.: 476,180

[22] Filed: Feb. 7, 1990

[30] Foreign Application Priority Data

Feb. 18, 1989 [DE] Fed. Rep. of Germany ....... 3904992

[51] Int. Cl.$^5$ ............................................. G01N 33/18
[52] U.S. Cl. .................................. 436/42; 204/153.22
[58] Field of Search ....................... 436/42; 204/153.22

[56] References Cited

U.S. PATENT DOCUMENTS

| | | | |
|---|---|---|---|
| 4,619,900 | 10/1986 | Scholz | 436/42 |
| 4,703,014 | 10/1987 | Fischer et al. | 436/42 |
| 4,720,464 | 1/1988 | Kuwata et al. | 436/42 |
| 4,802,957 | 2/1989 | Kuwata et al. | 436/42 X |
| 4,874,709 | 10/1989 | Fischer et al. | 436/42 |

*Primary Examiner*—Robert J. Hill, Jr.
*Attorney, Agent, or Firm*—Connolly and Hutz

[57] ABSTRACT

Reagent for the coulometric determination of water in a membrane-free cell, composed of an alcoholic solvent or solvent mixture in which imidazole and/or an imidazole derivative and/or diethanolamine and/or triethanolamine and sulphur dioxide and an iodide or plurality of iodides and optionally a conducting salt or plurality of conducting salts are dissolved. A membrane-free cell and method for the coulometric determination of water using this reagent are also disclosed.

15 Claims, No Drawings

REAGENT, CELL AND METHOD FOR THE COULOMETRIC DETERMINATION OF WATER

The invention relates to a reagent for the coulometric determination of water by the Karl Fischer reaction in a membrane-free cell.

A Karl Fischer reagent contains, for example, as reactive constituents methanol, sulphur dioxide, pyridine (Py) and iodine. The determination of water is then based on the so-called Karl Fisher reaction:

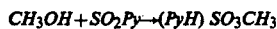

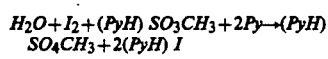

In this process, the first reaction step initially results in a salt of methylsulphurous acid, which is then oxidized after the second reaction step by iodine with the consumption of an equivalent amount of water.

The reagents intended for Karl Fischer coulometry contain an iodide instead of iodine. In Karl Fischer coulometry, the iodine necessary for the reaction is produced by anodic oxidation of the iodide. The water content is calculated from the current consumption for this oxidation reaction, i.e. the anode reaction has to proceed with 100% current efficiency.

However, the cathode reaction which proceeds in parallel produces by-products which can in turn again be oxidized by iodine and thus simulate water. The cathode reaction is therefore carried out in a separate cathode space which is separated from the anode space by a membrane. In this way, the interference with the anode reaction due to the products of the cathode reaction is reduced.

However, the interference is not completely eliminated since the cathodic reaction products slowly diffuse through the membrane. When the electric field is applied, anions migrate into the anode space. Both are oxidized in the anode space by iodine or at the anode and simulate water. Many Karl Fischer coulometers therefore have a so-called "drift" compensation which compensates for the diffusion in the current-free state. At the same time, there is no compensation for the migration of ions under the influence of the electric field. For this reason, in conventional Karl Fischer coulometry errors of up to 30% may occur which are caused by the migration of oxidizable anions. However, such errors have hitherto been tolerated because Karl Fischer coulometry is predominantly suitable for substance having low water contents (0.1 to 0.0001%) and exhibits particular advantages over other methods of determining water in the ppm range.

It is known that, to minimize the errors occurring in conventional Karl Fischer coulometry, two solutions of different composition are used in the anode space and in the cathode space which is separated under these circumstances by a membrane. The actual Karl Fischer reaction proceeds in the anolyte, whereas the catholyte is an auxiliary solution which makes a cathode reaction possible. The use of two electrolyte solutions of different composition or the use of a coulometric cell having a membrane is, however, cumbersome.

The object of the present invention is therefore to provide a reagent and a method for the coulometric determination of water by the Karl Fischer reaction whose application or implementation does not require a membrane.

The reagent according to the invention for the coulometric determination of water by the Karl Fischer reaction is composed of an alcoholic solvent or solvent mixture in which
sulphur dioxide,
imidazole and/or an imidazole derivative and/or diethanolamine and/or triethanolamine,
one or more iodides
and optionally one or more conducting salts are dissolved.

For the purpose of the present invention, an alcoholic solvent is understood to be a monohydric or dihydric alkanol which contains 1 to 3 carbon atoms and which may be substituted with 1 to 4 halogen atoms and/or 1 to 4 phenyl esters. The halogen atoms are bound to the carbon atoms of the alkanol which are free of hydroxyl groups. The phenyl radicals may in turn be mono-, di- or trisubstituted with halogen, ($C_1$ to $C_4$)alkyl and/or ($C_1$ to $C_4$)alkoxy. Monosubstituted phenyl radicals are preferred. A hydroxyl group of a dihydric alkanol may also be etherified with ($C_1$ to $C_4$)alkyl.

Possible halogen atoms for the substituents of the alkanol are bromine, iodine, fluorine and preferably chlorine atoms.

Examples of suitable alkanols are: methanol, ethanol, propanol, ethylene glycol, propylene glycol, 1,3-propanediol, 2-methoxyethanol, 2-chloroethanol, 2-bormoethanol, 2-iodoethanol, 2-fluoroethanol, 2,2,2-trifluoroethanol, 1-bromo-2-propanol, 2-chloro-1-propanol, 3-chloro-1,2-propanediol, 2,2,3,3-tetrafluoro-1-propanol, benzyl alcohol, 2-bromobenzyl alcohol, 3-methoxybenzyl alcohol, 4-methoxybenzyl alcohol, 4-methylbenzyl alcohol, 1-phenylethanol, 2-phenylethanol, 2-phenoxyethanol, benzhydrol and tetraphenylethanediol. The alkanols are used individually or, alternatively, mixed with one another. Optionally they are employed mixed with one or more other additional organic solvents, the amount of the alkanol being more than 10, preferably at least 25 per cent by weight of the solvent mixture.

Suitable as an additional solvent are, for example, aliphatic hydrocarbons containing 5 to 10 carbon atoms, preferably 6, 7 or 8 carbon atoms, or aromatic, optionally alkyl-substituted, preferably methyl-substituted hydrocarbons containing 6 to 12 carbon atoms preferably 6, 7 or 8 carbon atoms. Examples thereof are n-pentane, n-hexane, 2,3-dimethylbutane, 3-methylhexane, methylcyclopentane, n-heptane, cycloheptane, isooctane and decahydronaphthalene, and also benzene, toluene, 1,2-diethylenebenzene, xylene and 1,3-dimethylnapthalene. The following are furthermore suitable: aliphatic halogenated hydrocarbons containing 1 to 10 carbon atoms, preferably 1 to 7 carbon atoms, and aromatic halogenated hydrocarbons containing 6 to 10 carbon atoms, preferably 6 or 7 carbon atoms. Examples thereof are chloroform, dichloromethane, tetrachloromethane, 1,1,2,2-tetrachloroethane, 1,1,1-trichloroethane, 2-bromobutane, 1-bromo-3-chloropropane, 1-chlorohexane, 1,2-dibromo-1,1-dichloroethane, 1,2-dibromo-1,1-difluoroethane, 1,2-dichloroethane, 1,6-dichlorohexane, 2,2-dichloropropane, 1-fluoroheptane, pentachloroethane and prefluorobutyl iodide, and also chlorobenzene, 3-chlorotoluene, 4-bromochlorobenzene, 1,2-dibromobenzene, 1,4-difluorobenzene and 3-bromobenzotrifluoride.

The addition of an additional solvent serves primarily to improve the solution behaviour in the reagent according to the invention of certain samples (fats, oils and the like) to be examined.

Normally 0.05 to 5 mol, preferably 0.1 to 2 mol, of sulphur dioxide are dissolved in a litre of the reagent according to the invention.

As reactive base for the Karl Fischer reaction, the reagent according to the invention contains imidazole or an imidazole derivative, diethanolamine or triethanolamine. These bases may be contained individually or, alternatively, as a mixture.

As imidazole derivative, use is preferably made of a compound of the formula

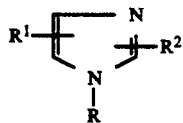

in which R, $R^1$ and $R^2$ are identical or different and in each case denote a hydrogen atom, a low alkyl radical preferably containing 1 to 4 carbon atoms or a phenyl radical, or $R^1$ and $R^2$ taken together also represent a condensed-on benzene nucleus and R has the stated meaning.

Examples of imidazole derivatives used according to the invention are 1-methylimidazole, 1-ethylimidazole, 1-propylimidazole, 1-butylimidazole, 2-methylimidazole, 2-ethylimidazole, 2-propylimidazole, 2-butylimidazole, 4-methylimidazole, 4-butylimidazole, 1,2-dimethylimidazole, 1,2,4-trimethylimidazole, 1-phenylimidazole, 2-phenylimidazole and benzimidazole.

For imidazole and the imidazole derivatives, the concentrations used in the reagent according to the invention are between 0.2 mol/l and 4 mol/l, and for diethanolamine and triethanolamine between 0.1 mol/l and 2 mol/l.

The reagent according to the invention contains, in addition, at least one soluble iodide which can be anodically oxidized to iodine and thus ensures that the Karl Fischer reaction proceeds. Alkali iodides or alkaline earth iodides such as, for example, sodium iodide, potassium iodide, lithium iodide, calcium iodide, can be used as soluble iodides. Hydroiodides of organic bases, for example of trimethylamine or triethylamine, are also suitable.

Preferably used are the hydroiodides of the reactive bases which are used in the reagent according to the invention, that is to say, for example, imidazole hydroiodide, 1-alkylimidazole hydroiodide, 2-alkylimidazole hydroiodide, diethanolamine hydroiodide or triethanolamine hydroiodide. The reagent according to the invention contains an iodide or a mixture of different iodides. The iodide concentration in the reagent according to the invention is between 0.02 mol/l and 1 mol/l. In the preparation of the reagent, the iodides may be added directly as salts or, alternatively, be prepared by reacting iodine with water in the finally formulated reagent.

The reagent according to the invention preferably contains one or more additional conducting salts to improve its conductance. The anions of these conducting salts may be derived from inorganic acids such as, for example, hydrogen halides, sulphuric acid, sulphurous acid, or from organic acids such as, for example benzoic acid and salicylic acid. The cations of the conducting salts may also be of an inorganic or organic nature. Inorganic cations are, for example, cations of alkali metals, in particular of lithium, sodium, potassium, caesium and the alkaline earth metals, in particular of calcium and barium. Halides such as sodium bromide, sodium iodide, potassium bromide, potassium iodide, caesium chloride, tetrabutyl bromide, calcium iodide, barium bromide, lithium benzoate or sodium salicylate are suitable. Preferably used are salts whose cations or anions are contained in the reagent according to the invention, for example imidazole hydrobromide, 1-methylimidazole hydrochloride, diethanolamine hydrochloride, diethanolammonium benzoate, imidazolinium salicylate, triethanolammonium methyl sulphite, imidazolinium methyl sulphite. Salts of the alkyl esters of sulphurous acid which are formed from sulphur dioxide and the alcohol used are also suitable as the iodides of the reactive bases used. Reaction products of the Karl Fischer reaction such as, for example, the alkyl sulphates of the bases contained, can also be used as conducting salts. The conducting salts may be added to the reagent during the preparation, but may also be produced during the preparation by reacting the co-reactants, for example the alkyl sulphates by reacting alcohol, sulphur dioxide and the corresponding base or the alkyl sulphates by oxidizing the alkyl sulphites by means of iodine in the presence of water.

In the normal case, the reagent according to the invention contains enough conducting salt for the electrical conductivity of the reagent at 20° C. t be at least 5 mS/cm, preferably 10 to 30 mS/cm.

In some cases, the iodides may also assume the function of a conducting salt. Normally, however, a conducting salt is used which is not an iodide. Preferably, bromides are used as conducting salts, in particular a hydrobromide of the reactive bases present in the reagent, that is to say, a hydrobromide of imidazole, of an imidazole derivative, of the diethanolamine or of the triethanolamine.

The reagent according to the invention is prepared by dissolving the components in the alcoholic solvent or solvent mixture, optionally while cooling to a temperature of 15° to 50° C., preferably to a temperature of 20° to 40° C. Normally 0.2 to 4 mol/l imidazole and/or imidazole derivative or 0.1 to 2 mol/l diethanolamine or triethanolamine are first dissolved in the alcoholic solvent or solvent mixture, and sulphur dioxide is introduced, for example, in an amount of 0.05 to 5 mol/l, preferably 0.1 to 2 mol/l. The iodide required is either added as such, or iodine and later water are added until discolouration occurs, as a result of which the iodine is formed. A conducting salt is optionally added to adjust the conductivity.

The reagent is used for the coulometric determination of water in solid or liquid substances by the Karl Fischer reaction in a membrane-free cell.

Substances whose water contents can be determined are, for example, fats, oils, organic solvents, pharmaceutical preparations etc.

The reagent according to the invention is poured into the membrane-free coulometric cell to a level such that the anode and cathode, and also the indicator electrode, are completely covered. The cathode may be formed from a platinum wire which is disposed at some distance from a platinum wire gauze serving as anode. The actual coulometric determination of water is carried out using the reagent according to the invention in a manner known per se.

The reagents according to the invention, which are convenient to handle, make possible Karl Fischer coulometry in a cell which does not have a separate cathode space. As a result, the interferences which are caused by the after-diffusion of oxidizable constituents from the cathode space into the anode space are completely eliminated.

EXAMPLE 1

102 g of imidazole (1.5 mol) are dissolved in 900 ml of methanol. 45 g of sulphur dioxide (0.7 mol) are introduced while cooling. Then 12.7 g of iodine (0.1 mol) are added. The solution is made up to 1 l with methanol. Then the iodine is reduced by dropwise addition of water until the colour of the solution changes to a faint yellow. In this process, imidazole hydroiodide and imidazole methyl sulphate are produced as conducting salts. The electrical conductivity at 20° C. mS/cm.

EXAMPLE 2

66 g of methylimidazole (0.8 mol) are dissolved in 900 ml of 2-chloroethanol. Then 26 g of sulphur dioxide (0.4 mol) are introduced while cooling. Subsequently 42 g of 2-methylimidazole hydroiodide (0.2 mol) and 98 g of 2-methylimidazole hydrobromide (0.6 mol) are added. The solution is made up to a total volume of 1 l with 2-chloroethanol and dehydrated by adding about 0.5 g of iodine.

EXAMPLE 3

42 g of diethanolamine (0.4 mol) are dissolved in 800 ml of methanol. Then 26 g of sulphur dioxide (0.4 mol) are introduced. 47 g of diethanolamine hydroiodide (−0.2 mol) and 59.5 g of imidazole hydrobromide (=0.4 mol) are added to this solution. The solution is made up to 1 l with methanol. The electrical conductivity at 20° C. is 28 mS/cm.

EXAMPLE 4

116 g of diethanolamine (1.1 mol), 14 g of imidazole (0.2 mol) and 59 g of imidazole hydroiodide (0.3 mol) are dissolved in 800 ml of methanol. Then 65 g of sulphur dioxide (1 mol) are introduced while cooling. Finally, 25.4 g of iodine (0.2 mol) are added. The solution is made up to 1 l with methanol and decolourized by dropwise addition of water. The electrical conductivity at 20° C. is 28 mS/cm.

EXAMPLE 5

105 g of diethanolamine (1 mol), 163 g of diethanolamine hydroiodide (0.7 mol) and 41 g of salicylic acid (0.3 mol) are dissolved in 600 ml of methanol and 300 ml of chloroform. Then 51 g of sulphur dioxide (=0.8 mol) are introduced while cooling. The solution is made up to 1 l with methanol. The electrical conductivity at 20° C. is 11 mS/cm.

EXAMPLE 6

126 g of diethanolamine (1.2 mol), 12.7 g of iodine (0.1 mol) and 74 g of imidazole hydrobromide (0.5 mol) and 80.5 g of tetrabutylammonium bromide (0.25 mol) are dissolved in 500 ml of methanol an 200 ml of toluene. Then 64 g of sulphur dioxide (1.0 mol) are introduced. The solution is made up to 1 l with methanol and decolourized by dropwise addition of water. The electrical conductivity at 20° C. is 17 mS/cm.

EXAMPLE 7

A commercially available Karl Fischer coulometer ®Metrohm 652 of the firm of Metrohm AG, Herisau, Switzerland, is equipped with a membrane-free cell. The cell is filled with the reagent according to Example 1. The device is switched on in order to remove any entrained water from the cell and from the reagent by automatic preconditioning. After preconditioning, the determination is started and a sample of 1.00 ml of 1-propanol is injected into the cell using a hypodermic syringe. After about 3 minutes the device indicates a water content of 0.0633%. The actual water content is 0.0630%.

What is claimed is:

1. A reagent for the coulometric determination of water in a membrane-free cell, comprising an alcoholic solvent in which a reactive base constituent selected from the group consisting of imidazole, imidazole derivatives, diethanolamine, triethanolamine and mixtures thereof, together with sulphur dioxide, an iodide and a conducting salt constituent selected from the group of imidazole hydrobromide, imidazole derivative hydrobromide, diethanolamine hydrobromide, triethanolamine hydrobromide and mixtures thereof are dissolved.

2. A reagent according to claim 1, wherein said alcoholic solvent is a mixture of alcohol solvents.

3. A reagent according to claim 1, wherein said iodide consists of a plurality of iodides.

4. A reagent according to claim 1, characterized in that it contains 0.2 to 4 mol/l of at least one of said imidazole and imidazole derivatives.

5. A reagent according to claim 1, containing 0.05 to 5 mol/l sulphur dioxide.

6. A reagent according to claim 5, containing 0.1 to 2 mol/l sulphur dioxide.

7. A reagent according to claim 1, containing 0.02 to 1 mol/l of iodide.

8. A reagent according to claim 1, containing a sufficient amount of said conducting salt for its electrical conductivity to be at least 5 mS/cm at 20° C.

9. A reagent according to claim 8, containing a sufficient amount of conducting salt for its electrical conductivity to be 10 to 30 mS/cm at 20° C.

10. A reagent according to claim 1, characterized in that it contains 0.1 mol/l to 2 mol/l of at least one of said diethanolamine and triethanolamine.

11. A reagent according to claim 1, characterized in that it contains one or more other additional organic solvents selected from the group consisting of aliphatic hydrocarbons containing 5 to 10 carbon atoms, aromatic hydrocarbons containing 6 to 12 carbon atoms, aliphatic halogenated hydrocarbons containing 1 to 10 carbon atoms and aromatic halogenated hydrocarbons containing 6 to 10 carbon atoms.

12. A membrane-free cell for the coulometric determination of water by the Karl Fischer reaction containing the reagent set forth in claim 1.

13. A method for the coulometric determination of water by the Karl Fischer reaction i a membrane-free cell using a Karl Fischer reagent, characterized in that the Karl Fischer reagent used in the membrane-free cell comprises the reagent set forth in claim 1.

14. A method for the coulometric determination of water by the Karl Fischer reaction in a membrane-free cell using a Karl Fischer reagent, characterized in that a Karl Fischer reagent is used comprising an alcoholic solvent in which a reactive base constituent selected from the group consisting of imidazole, imidazole derivatives, diethanolamine, triethanolamine and mixtures thereof, together with sulphur dioxide and an iodide are dissolved.

15. A method for the coulometric determination of water by Karl Fischer reaction in a membrane-free cell using a Karl Fischer reagent, characterized in that the Karl Fischer reagent used in the membrane-free cell comprises an alcoholic solvent in which a reactive base constituent selected from the group consisting of imidazole, imidazole derivatives, diethanolamine, triethanolamine and mixtures thereof, together with sulphur dioxide, an iodide and one or more conducting salts are dissolved.

* * * * *